United States Patent [19]
Halperin et al.

[11] Patent Number: 5,683,356
[45] Date of Patent: Nov. 4, 1997

[54] METHOD AND COMPOSITION FOR REMOVAL OF EXCESS HYDROGEN IONS FROM HUMANS

[75] Inventors: Mitchell Lewis Halperin, North York; Surinder Cheema-Dhadli, Mississauga, both of Canada

[73] Assignee: Rossmark Medical Publishers Inc., Sterling, Canada

[21] Appl. No.: 673,137

[22] Filed: Jul. 1, 1996

Related U.S. Application Data

[63] Continuation-in-part of Ser. No. 197,949, Feb. 17, 1994, Pat. No. 5,533,964.

[51] Int. Cl.$^6$ .................................................. A61M 37/00
[52] U.S. Cl. ................................. 604/4; 604/5; 128/898
[58] Field of Search .......................... 604/4, 5; 128/898

[56] References Cited

U.S. PATENT DOCUMENTS

| | | |
|---|---|---|
| 400,491 | 4/1889 | Ross . |
| 3,953,329 | 4/1976 | Updike . |
| 3,994,799 | 11/1976 | Yao et al. . |
| 4,007,138 | 2/1977 | Kanig . |
| 4,405,596 | 9/1983 | Helbig et al. . |
| 4,435,176 | 3/1984 | Ishikawa . |
| 4,878,891 | 11/1989 | Judy et al. . |
| 5,019,096 | 5/1991 | Fox, Jr. et al. . |
| 5,533,964 | 7/1996 | Halperin et al. ........................ 604/4 |

FOREIGN PATENT DOCUMENTS 9522337  8/1995  WIPO .

OTHER PUBLICATIONS

Database WPI, Section Ch, Week 9007, Derwent Publications Ltd., London, GB; Class E37, AN 90-047474.

"Alkali therapy extends the period of survival during hypoxia: studies in rats", *American Journal of Physiology*, Halperin Frank et al, to be published circa Jul./Aug. 1996.

*Primary Examiner*—Paul B. Prebilic
*Attorney, Agent, or Firm*—Riches, McKenzie & Herbert

[57] ABSTRACT

A compound or composition incorporating silver carbonate is for use in removing excess hydrogen ions in a patient. The silver carbonate reacts with chloride ions which naturally occur in the patient's body fluids to produce a silver chloride precipitate. The chemical reaction producing silver chloride causes the release of hydroxyl, carbonate and/or bicarbonate ions which react with free hydrogen ions to form carbon dioxide and water. The silver carbonate compound or composition may be provided in a blood filtration cartridge, syringe or an orally ingestible form either alone or surrounded by a selectively permeable membrane. The membrane is selected to permit movement of ions, as well as carbon dioxide and water molecules therethrough, while preventing the silver carbonate or silver chloride precipitate from being released into the patient.

20 Claims, 2 Drawing Sheets

METHOD AND COMPOSITION FOR REMOVAL OF EXCESS HYDROGEN IONS FROM HUMANS

RELATED APPLICATIONS

This application is a continuation-in-part application of U.S. patent application Ser. No. 08/197,949, filed Feb. 17, 1994 and entitled "Composition and Apparatus for Removal of Excess Hydrogen Ions from Humans", and which issued to U.S. Pat. No. 5,533,964 on Jul. 9, 1996.

SCOPE OF THE INVENTION

This invention relates generally to a novel compound or composition which may be used to remove hydrogen ions ($H^+$) from a patient. Hydrogen ions are generated in the patient, in response to such conditions as heart attack, poor renal function, acute renal failure and other medical conditions and can cause further damage to the patient. More particularly, the invention relates to a compound/composition which removes chloride ions and replaces them with hydroxyl, carbonate and/or bicarbonate ions released from binding with the compound/composition. These alkaline anions will react with freehydrogen ions to produce $H_2O$ and $CO_2$ as the sole by-products. The present inventors have discovered that by the use of $Ag_2CO_3$ as a compound or in a composition, the silver ions ($Ag^+$) bond with the free chloride ions ($Cl^-$) to release carbonate ions ($CO_3^=$) which then bind with the free excess hydrogen ions ($H^+$), without introducing potentially harmful cations or anions to the patient.

BACKGROUND OF THE INVENTION

Excess hydrogen ions ($H^+$) are generated and retained in an individual as a result of a heart attack, poor renal function or other maladies, and have a serious and deleterious affect on the individual's health.

The conventional treatment in removing such excess of hydrogen ions ($H^+$) involves the administration of sodium bicarbonate ($NaHCO_3$) or sodium carbonate ($Na_2CO_3$), alone or in combination. The carbonate ($CO_3^=$) and bicarbonate ions ($HCO_3^-$) react with free hydrogen ions ($H^+$) to produce $H_2O$ and $CO_2$, but also release at the same time, free sodium ions ($Na^+$). A major disadvantage of the conventional administration of sodium bicarbonate to reduce the number of free hydrogen ions ($H^+$) is that the amount of $NaHCO_3$ or $Na_2CO_3$ which can be safely administered is limited, because free sodium ions ($Na^+$) in large concentrations or content may be harmful to the patient.

HEART ATTACK PATIENTS

The human body needs adenosinetriphospate (ATP) as useful energy so that the body can perform biologic work. To permit this work, ATP must be converted to adenosinediphosphate (ADP). In a healthy individual, the body's regeneration of needed ATP predominantly occurs by the consumption of oxygen ($O_2$) through the tricarboxylic acid (TCA) cycle and the electron transport pathway (ETP), as for example, is described at pages 215 to 222 of *Clinical Detective Stories*, Halperin, M. L. and Rolleston, F. S., Portland Press, 1993. The TCA cycle oxidizes acetyl groups (found in acetyl-CoA) to yield the useful products NADH (nicotinamide adenine dinucleotide ($AND^+$) having a hydrogen ion ($H^+$) bound thereto) and $FADH_2$ (flavine adenine dinucleotide), the ETP oxidizes the hydrogen atoms in the NADH or $FADH_2$ molecule to form $H_2O$, with the production of ATP.

Acute episodes of poor heart performance lead to the rapid deterioration and eventual death of a patient when the heart fails to pump enough oxygenated blood to vital organs. Hypoxia, a deficiency of oxygen reaching these vital organs of the body, forces tissues to regenerate their ATP from anaerobic glycolysis (the conversion of glucose to lactic acid ($L^-+H^+$)). Anaerobic glycolysis yields two molecules of ATP plus two molecules of lactic acid ($L^-+H^+$) per molecule of glucose consumed. As such, hypoxia prevents the oxidation of the hydrogen atoms on NADH to yield ATP and causes the rapid formation of lactic acid ($L^-+H^+$).

Complete oxidation of glucose to $CO_2$ and $H_2O$ via glycolysis, pyruvate dehydrogenase (PDH), and the ATP generation system yields 36 to 40 ATP per glucose. Anaerobic glycolysis must therefore use glucose 18 to 20 times faster than complete oxidation to meet the normal demands of a tissue for regeneration of ATP. As such, this pathway must produce hydrogen ions ($H^+$) at a very rapid rate.

To keep a patient having a heart attack alive long enough to allow for more formal intervention, an alkali is administered to offset the hydrogen ion ($H^+$) build up. Typically, alkaline salts composed of a sodium cation ($Na^+$) together with a $H^+$ acceptor, such as bicarbonates ($HCO_3^-$), carbonates ($CO_3^=$), hydroxyl ions ($OH^-$) or other $H^+$ acceptors. This treatment can prolong the period of survival during hypoxia (Halperin et al, Amer. J. Physiology: 1996 in press).

ACUTE RENAL FAILURE/POOR RENAL FUNCTION

The kidneys act to eliminate hydrogen ions ($H^+$) from the body. Patient's experiencing acute renal failure or even poor renal function, may also develop excessive levels of hydrogen ions ($H^+$) in their bodies.

CONVENTIONAL TREATMENT $NaHCO_3$ is by far most widely used as a treatment to remove excess hydrogen ions, which on implementation results in the following chemical reaction:

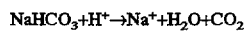

$$NaHCO_3 + H^+ \rightarrow Na^+ + H_2O + CO_2$$

By the administration of conventional treatments, excess amounts of $Na^+$ ions are introduced into the patient. Sodium ions are particularly disadvantageous as sodium tends to pool in the fluid outside cells, and of special importance in the patient's lungs, and if present in sufficiently large amounts, may lead to death.

As a practical matter therefore, there are limits to the amount of $NaHCO_3$ (or other conventional buffering compositions) which may be safely administered. The net result is a corresponding limit to the concentration of free hydrogen ions ($H^+$) which may be safely removed.

SUMMARY OF THE INVENTION

It is therefore an object of the invention to provide a compound or composition which acts to bind excess free hydrogen ions ($H^+$) which occur in a patient as a result of a heart attack, poor renal function, acute renal failure or other medical conditions, and which when administered, does not introduce quantities of cations which may produce a particular disadvantage to the patient.

Another objective of the invention is to provide a compound or composition which, in use, substitutes a bicarbonate, carbonate or hydroxyl ion for chloride ions ($Cl^-$) which naturally occur throughout the patient's body.

A further object of the invention is to provide a composition which binds with free hydrogen ions ($H^+$) to produce $H_2O$ and $CO_2$, and which leaves substantially no undesired residue in the patient.

A further object of the invention is to provide a method, apparatus or kit for use in filtering and removing excess $H^+$ ions from a patient's body which does not alter the cation composition of the body.

In accordance with the present invention, the applicant has discovered that the compound $Ag_2CO_3$ or $AgHCO_3$ as part of a composition in solid form may be advantageously used either in vitro or in vivo to reduce the concentration of free hydrogen ions ($H^+$) in a patient without introducing harmful excess cations.

By providing $Ag_2CO_3$ in solid form, the silver cation $Ag^+$ from the solid or composition is found to react avidly and specifically with chloride ions ($Cl^-$) which naturally occur in the patient's body under the reaction:

(i) $2Cl^- + Ag_2CO_3 \rightarrow 2AgCl + CO_3^=$

The carbonate ion ($CO_3^=$) freed by this reaction then bonds with free excess hydrogen ions ($H^+$) in the patient's fluids by the chemical reaction:

(ii) $CO_3^= + H^+ \rightarrow HCO_3^-$ and (iii) $HCO_3^- + H^+ \rightarrow H_2O + CO_2$ Silver has not previously been considered for use in compositions/compounds out of concern that free silver ions ($Ag^+$) introduced into the patient may be deleterious to the patient's health. The applicant has discovered however, that with the compound/composition of the present invention, free silver ions ($Ag^+$) bind with free chloride ions ($Cl^-$) derived from a patient's body to form a highly insoluble silver chloride precipitate which does not adversely affect the patient.

As the AgCl has an extremely low solubility, it exists almost entirely as a solid precipitate with virtually no free silver ions ($Ag^+$) released into the patient. Free hydrogen ions ($H^+$) in the patient combine with the released carbonate ($CO_3^=$) or hydrogen carbonate ($HCO_3^-$) ions, yielding water and carbon dioxide, with no increase in excess cations in the patients.

In another embodiment, a composition comprising resin and $Ag_2CO_3$ is used in place of simply the solid $Ag_2CO_3$ compound/composition. The resin is preferably a cation exchange resin, as for example Dowex—1 (ionic from $OH^-$) or Dowex macroporous (ionic form $OH^-$, $CO_3^=$ or $HCO_3^-$). The patient's blood, plasma or body fluids may be extracted through a selectively permeable membrane, as a natural cellulose membrane, and passed through the ion exchange resin. As free chloride ions ($Cl^-$) naturally present in the plasma or fluids bond with the silver ions ($Ag^+$) or with the resin, carbonate ions ($CO_3^=$), bicarbonate ions ($HCO_3^-$) and/or hydroxyl ions ($OH^-$) are released into the plasma or fluids under the reactions:

(iv) $2Cl^- + Resin.CO_3 \rightarrow Resin.Cl + CO_3^=$ (v) $Cl^- + Resin.HCO_3 \rightarrow Resin.Cl + HCO_3^-$ (vi) $Cl^- + Resin.OH \rightarrow Resin.Cl + OH^-$ The carbonate ions ($CO_3^=$), or bicarbonate ions ($HCO_3^-$) then react with free hydrogen ions ($H^+$) as previously described in reactions (ii) and (iii) producing water and carbon dioxide. Hydroxyl ions ($OH^-$) react with free hydrogen ions ($H^+$) to produce water by the reaction:

(vii) $OH^- + H^+ \rightarrow H_2O$

In a further embodiment, the composition resin/$Ag_2CO_3$ or solid $Ag_2CO_3$ compound may be provided for oral ingestion, for ion exchange within the gastrointestinal tract. Preferably such a compound or composition would be provided either alone in solid form, or within a selectively permeable membrane, such as a natural cellulose membrane, which would allow substantially unhindered transmission of fluids together with $Cl^-$, $CO_3^=$, $OH^-$, and $HCO_3^-$ ions therethrough.

Accordingly in one aspect the present invention resides in either a buffering compound which comprises $Ag_2CO_3$ or a composition which comprises solid $Ag_2CO_3$ and a carrier.

In another aspect the present invention resides in a kit for use in buffering excess hydrogen ions in a patient, the kit comprising either a buffering compound comprising $Ag_2CO_3$ or a buffering composition comprising $Ag_2CO_3$ with or without a resin, and means for selectively permitting ion flow between a patient's body fluid and the buffering compound or composition while preventing movement of the buffering compound into the fluid.

In another aspect the present invention resides in a method of removing excess hydrogen ions in a patient's body fluid comprising, contacting said body fluid with hydrogen ion buffering means for bonding with free anions naturally present in said fluid and substituting therefore buffering ions which bond with said hydrogen ions to produce water and carbon dioxide molecules, said buffering means selected from the group consisting of a compound comprising $Ag_2CO_3$ in solid form and a composition comprising $Ag_2CO_3$.

In another aspect the present invention resides in an apparatus for use in buffering excess hydrogen ions in a patient's blood, the apparatus comprising a housing having a reaction chamber and a blood chamber, the reaction chamber separated from the blood chamber by a membrane, a buffering compound comprising $Ag_2CO_3$ disposed in the reaction chamber, wherein the membrane is selectively permeable to permit the passage of free ions therethrough while preventing movement of said compound, plasma proteins and red blood cells thereacross.

In a further aspect the present invention resides in a syringe or cartridge for use in buffering excess hydrogen ions in a patient's blood, the syringe comprising a housing having a reaction chamber and a blood chamber, said reaction chamber separated from said blood chamber by a membrane disposed across said housing, a buffering composition comprising $Ag_2CO_3$ and a resin disposed in the reaction chamber, the membrane selectively permeable to permit the movement of free ions therethrough while preventing movement of said composition, plasma proteins and red blood cells thereacross, means for drawing a quantity of blood into the blood chamber and then reintroducing the blood into said patient.

In another aspect the membrane is preferably a natural cellulose membrane.

DETAILED DESCRIPTION

Figure 1:
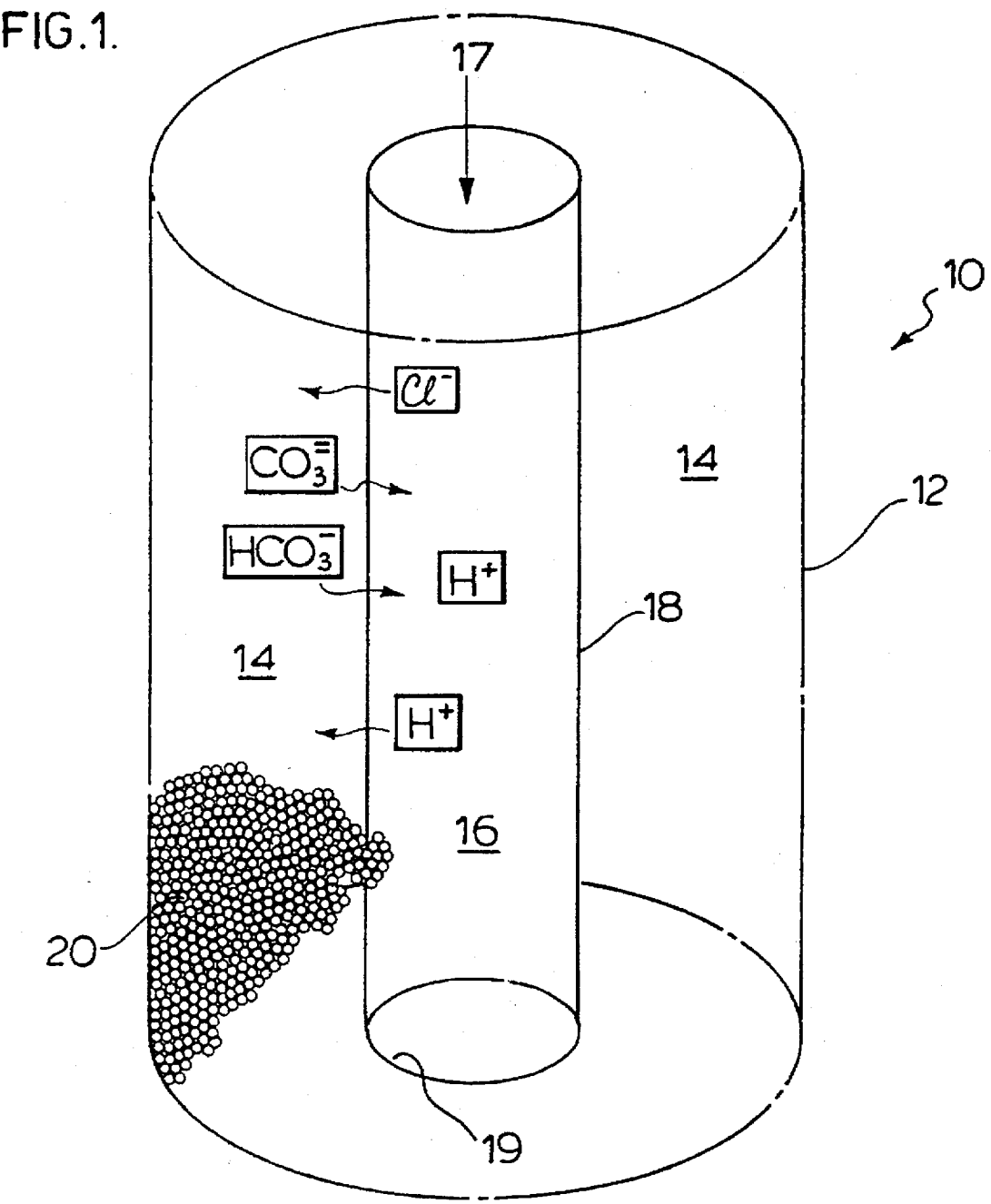
FIG. 1 is a schematic view of a filter cartridge for use in accordance with a first aspect of the invention.

It has been discovered that either a compound or composition comprising $Ag_2CO_3$ in solid form may advantageously be used to treat patients having unduly high concentrations of hydrogen ions ($H^+$) in their body as a result of heart attack, acute renal kidney/poor renal function failure or other medical conditions.

The applicants have found, that on contacting body fluids with $Ag_2CO_3$, free chloride ions ($Cl^-$) present naturally in the body fluids advantageously combine with silver ions ($Ag^+$) which exist in an almost instantaneous equilibrium with the solid $Ag_2CO_3$ to produce a solid precipitate by the reaction:

$$2Cl^- + Ag_2CO_3 \rightarrow 2AgCl + CO_3^-$$

The carbonate ion ($CO_3^=$) released by the reaction bond with free hydrogen ions ($H^+$) in the patient's fluids by the reactions:

(ii) $H^+ + HCO_3^= \rightarrow HCO_3^-$ (iii) $H^+ + HCO_3^- \rightarrow H_2O + CO_2$ By reactions (ii) and (iii) the molar concentration of free hydrogen ions ($H^+$) in the patient may be reduced by binding the hydrogen ions in water molecules. Further, as the silver cation ($Ag^+$) bonds with free chloride ions ($Cl^-$) aggressively to form a precipitate, harmful concentrations of free silver cations ($Ag^+$) are not introduced into the patient.

$Ag_2CO_3$ is particularly suitable for the present invention as $Ag_2CO_3$ exists in equilibrium with a very fast and almost simultaneous existence with free $Ag^+$ ions and $CO_3^=$ ions. As such, free silver ions ($Ag^+$) tend to bond almost immediately with chloride ions ($Cl^-$), forming the desired carbonate ions ($CO_3^=$), or bicarbonate ions ($HCO_3^-$).

$Ag_2CO_3$ has an extremely low solubility in water of less than 0.0032 grams/100 cc in cold water. Once the silver ions ($Ag^+$) have bonded with $Cl^-$ ions, the resulting AgCl forms a solid precipitate having a still lower solubility of less then 0.000089 grams/100 cc in cold water. As such, by the use of $Ag_2CO_3$ there is minimal likelihood that free silver ions ($Ag^+$) would exist in solution so as to adversely affect the patient's health. The lower solubility of the resulting precipitate AgCl advantageously reduces the likelihood of the reaction reversing to free chloride ions ($Cl^-$) and silver ions ($Ag^+$) once the AgCl precipitate has formed.

The insolubility of the resulting precipitate further advantageously permits the use of the $Ag_2CO_3$ compound or composition with selectively permeable membranes, and preferably membranes which permit the passage therethrough of small molecular weight compounds and not larger molecular compounds.

While $Ag_2CO_3$ as a solid compound or composition may be used to achieve the objects of the present invention, $Ag_2CO_3$ in other forms may also be used. $Ag_2CO_3$ may be provided as part of a composition together with a carrier. In one embodiment the carrier preferably is a solid impregnated with or bound to $Ag_2CO_3$. Plasma or other fluids from a patient, may be contacted with the absorbed or bound $Ag_2CO_3$ composition. On contact, chloride ions ($Cl^-$) in the body fluids bond with silver ions ($Ag^+$) present on the carrier by the reaction:

(iv) $Cl^- + Carrier.HCO_3 \rightarrow Carrier.Cl + HCO_3^-$ the bicarbonate ion ($HCO_3^-$) then binds with free hydrogen ions ($H^+$) in the patient's body fluids to reduce the molar concentration of free hydrogen ions by the reaction:

$$H^+ + HCO_3^- \rightarrow H_2O + CO_2$$

Carriers particularly suitable for use with the present invention include dextran, agarose, cellulose, and polystyrene, such as those sold under the trade names Dowex anion exchangers.

In another embodiment the $Ag_2CO_3$ composition, either alone or in combination with a suitable carrier, is encapsulated or retained within a structure, such as a selectively permeable membrane. The selectively permeable membrane is chosen to permit the transmission of ions therethrough while preventing the passage of solid $Ag_2CO_3$ or the resulting precipitate AgCl therethrough. Suitable selectively permeable membranes include pure regenerated natural cellulose membranes, such as those sold under the trade name Spectra/Por membranes.

As is to be appreciated, as buffering carbonate ($CO_3^=$) or bicarbonate ions ($HCO_3^-$) are released on the silver ions ($Ag^+$) bonding with chloride ions ($Cl^-$) to form the highly insoluble precipitate AgCl, almost no free cations are released by the reactions. As such by the use of the present invention, buffering ions may be provided to bond with hydrogen ions ($H^+$) with virtually no increase in harmful cations such as $Na^+$ in the patient.

While a resin has been disclosed as a component of a preferred composition, it is to be appreciated that other carriers may equally be used.

There are several possible uses for the compound or composition of the present invention in the treatment of patients. The following are provided by way of example only, and are not intended to be limiting.

EXAMPLE 1

Heart Attack Patients

The present invention may advantageously be used in the treatment of heart attack patients.

Where a patient has undergone a heart attack and oxygenated blood is circulating too slowly, solid $Ag_2CO_3$ as either a compound or in a carrier form may be used to reduce free hydrogen ions ($H^+$) in the patient's body, and provide a longer period of time in which other medical strategies to restart the heart may be taken.

A first embodiment of an apparatus for use with a compound comprising $Ag_2CO_3$ is best shown in FIG. 1.

FIG. 1 shows a blood filtration cartridge 10 characterized by a fluid impermeable chemically inert plastic outer housing 12. The interior of the housing 12 is divided into essentially two areas, a reaction chamber 14, and a centrally disposed blood passage chamber 16. The reaction chamber 14 is delineated from the blood passage chamber 16 by a selectively permeable membrane 18. A reactant compound 20 comprising $Ag_2CO_3$ is provided in the reaction chamber 14.

The selectively permeable membrane 18 is chosen to permit free passage of water and ions from the blood to move across the membrane 18 into and from the reaction chamber 14. The membrane 18 is further selected to prevent the movement of blood cells and proteins from the blood passage chamber 16 into the reaction chamber 14, or the movement of solid $Ag_2CO_3$ or the resulting AgCl precipitate from the reaction chamber 14 into the blood passage chamber 16.

In use, blood from a patient is extracted and pumped by a pump (not shown) through the cartridge 10 via passage inlet 17. As the blood enters the passage 16, the aqueous phase of blood containing chloride ions ($Cl^-$) and hydrogen ions ($H^+$) selectively pass through the membrane 18 into the reaction chamber 14. In the reactive chamber 14, buffering ions are freed on the chloride ions (Cl⁻) forming a preferential bond with free silver ions (Ag⁺) existing in rapid equilibrium with $Ag_2CO_3$. The result of the chloride ions (Cl⁻) bonding with free silver ions (Ag⁺) is the formation of the substantially insoluble precipitate AgCl in the reaction chamber 14 by the reaction:

(i) $Ag_2CO_3 + 2Cl^- \rightarrow 2AgCl + CO_3^-$

As the chloride ions (Cl⁻) bond with any available free silver ions (Ag⁺), buffering carbonate ions ($CO_3^=$) and bicarbonate ions ($HCO_3^-$) are released. These released buffering ions either bond with free hydrogen ions (H⁺) in the aqueous phase of the blood which has passed into the reaction chamber 14, or move through the membrane 18 into the blood passage chamber 16 to bond with free hydrogen ions (H⁺) in the patient's blood by the reactions:

(ii) $CO_3^- + H^+ \rightarrow HCO_3^-$ and (iii) $HCO_3^- + H^+ \rightarrow H_2O + CO_2$ In this manner, the concentration of free hydrogen ions (H⁺) in the patient's blood can be reduced with virtually no cations being introduced into the patient's blood.

The treated blood is then pumped outwardly from the cartridge 10, via passage outlet 19 for reintroduction into the patient.

The removal of hydrogen ions (H⁺) occurs in a 1:1 stoichiometric ratio with $HCO_3^-$ or $OH^-$ ions and a 2:1 stoichiometric ratio with $CO_3^{2-}$ ions. As such, a given amount of $Ag_2CO_3$ will yield a particular "dosage" for removing a given amount of hydrogen ions (H⁺). In this manner a given quantity of $Ag_2CO_3$ may be provided in the cartridge 10 to buffer a given amount of hydrogen ions (H⁺).

Figure 2:
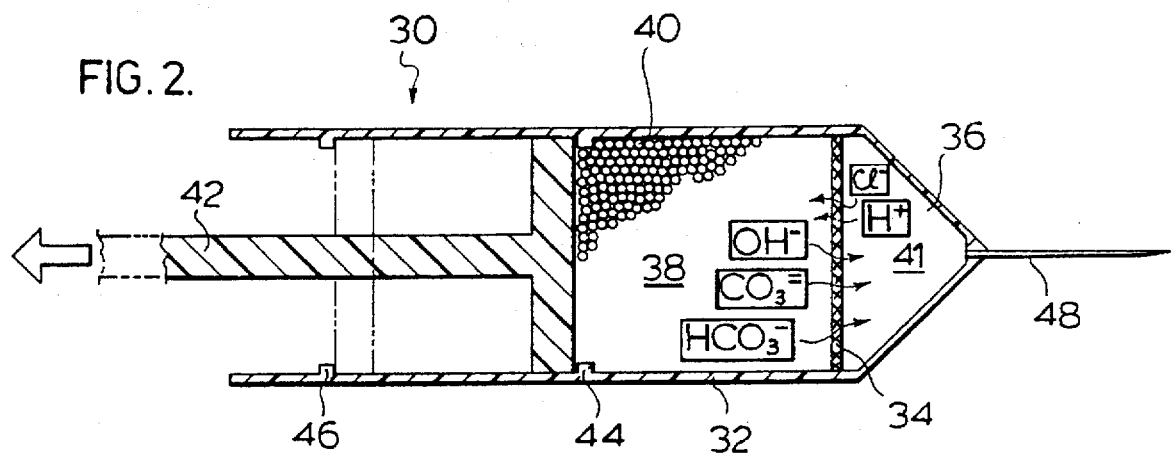
FIG. 2 is a schematic view of a syringe for use in accordance with a second aspect of the invention.

Reference may be made to FIG. 2 which shows schematically a second embodiment of the invention. FIG. 2 shows a syringe 30 adapted for portable use, as for example as part of a kit for buffering free hydrogen ions (H⁺) from a heart attack patient's blood 41. The syringe 30 is particularly suited for field use, as for example by a paramedic, prior to the patient's arrival at a hospital.

The syringe 30 is constructed on the same principles as the cartridge 10 shown in FIG. 1. The syringe 30 comprises a chemically inert housing 32, plunger 42 and needle 48. The syringe housing 32 is divided by a selectively permeable membrane 34 to delineate a blood chamber 36 and a reaction chamber 38. Microencapsulated reactant 40 is provided within the reaction chamber 38. The reactant 40 preferably is a composition comprising $Ag_2CO_3$ and a carrier.

The membrane 34 is chosen to selectively prevent red blood cells and plasma proteins in blood 41 which has been drawn into the syringe 30 to pass therethrough into a reaction chamber 38, while permitting passage of water and ions thereacross. It is to be understood that the membrane 34 is secured in position in sealing contact with the syringe 30. While FIG. 2 shows the attachment of the membrane 34 schematically, it is to be appreciated that the syringe 30 would include sufficient supporting structures for the membrane 34 to withstand pressure differentials provided on sliding of the plunger 42. Such supporting structures are not shown in the schematic but would be appreciated as including rims which grip the peripheral edge of the membrane 34, perforated disks which sandwich the membrane 34 therebetween or other support structures which will now become apparent.

Inner and outer annular stop rings 44,46 may be provided about the inner surface of the syringe housing 32 to limit inward and outward axial sliding of the plunger 42. The inner stop ring 44 advantageously acts to prevent the plunger 42 from being slid too far inwardly into the housing 32. Inward movement of the plunger 42 is limited to prevent the solid reactant 40 from being forced into contact with the membrane 34, whereby the membrane 34 may be damaged and reactant 40 may move into the blood chamber 36 or the patient. Outer annular flange 46 advantageously prevents the inadvertent complete withdrawal of the plunger 42 from the housing 32.

Although not essential, the interior of the syringe 36 may be maintained under a vacuum or filled with a sterile isotonic solution of sodium bicarbonate so as to minimize the possibility of introducing air bubbles into the patient's blood.

In operation of the syringe 30, the needle 48 is inserted into a patient, and the plunger 42 is slid outwardly from the syringe housing 32, drawing a quantity of blood 41 into the blood chamber 36 for buffering. As blood 41 is drawn from the patient, water, free chloride ions (Cl⁻) in the blood pass through the membrane 34 into the reaction chamber 38.

In the manner previously described with reference to FIG. 1, chloride ions (Cl⁻) from the patient which have moved into the reaction chamber 38 bond with free silver ions (Ag⁺) to produce an insoluble AgCl precipitate. As the free silver ions (Ag⁺) bond with the chloride ions (Cl⁻), carbonate ions ($CO_3^=$), hydroxyl ($OH^-$) ions or bicarbonate ions ($HCO_3^-$) are released. By reactions (ii), (iii) or (vii) described previously, the bicarbonate ($HCO_3^-$), hydroxyl ($OH^-$) and carbonate ions ($CO_3^=$) bond with either free hydrogen ions (H⁺) which have passed through the membrane 34 into the reaction chamber 38, or themselves pass through the selectively permeable membrane 34 to bond with hydrogen ions (H⁺) in the blood chamber 36.

The treated blood 41 having a reduced concentration of free hydrogen ions (H⁺) and any remaining free buffering ions ($CO_3^=$, $OH^-$, $HCO_3^-$) may then be reintroduced into the patient by sliding the plunger 42 axially inwardly to a position abutting the stop ring 44.

The syringe 30 may contain a sufficiently large amount of microencapsulated reactant 40, such that in use, the plunger 42 may be repeated moved to withdraw, treat and then reinject blood 41 into a patient; this enables an exact amount of Cl⁻ ion removal and $HCO_3^-$ ion replacement.

EXAMPLE 2

Kidney Patients

The compound of the present invention may be used in vivo to reduce undesirable concentrations of excess free hydrogen ions (H⁺) in patients who have either experienced acute renal failure or who have poor renal function.

As the human stomach secretes naturally both hydrogen ions (H⁺) and chloride ions (Cl⁻), it is possible to provide for oral ingestion either a compound or composition comprising $Ag_2CO_3$.

Figure 3:
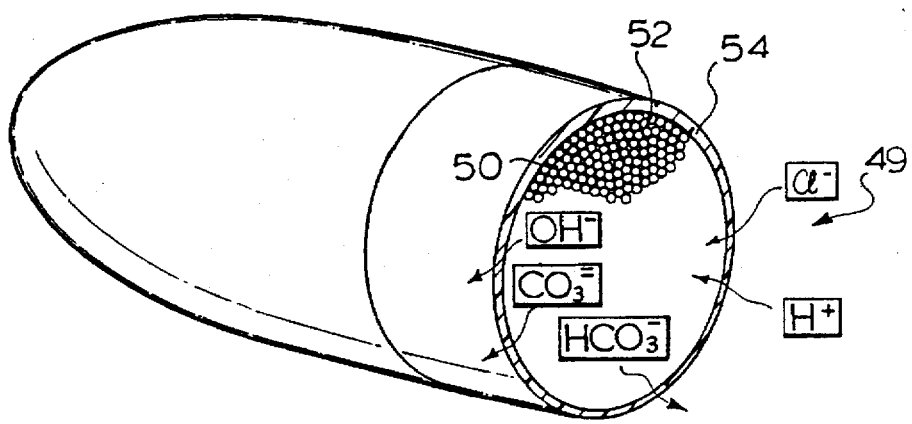
FIG. 3 is a cut-away perspective view of a capsule for use in accordance with a third aspect of the invention.

To remove excess hydrogen ions (H⁺), a quantity of $Ag_2CO_3$ is ingested either as a solid compound, or more preferably and seen in FIG. 3, as a capsule 49 of solid reactant 50 comprising $Ag_2CO_3$ microencapsulated within a carrier 52. The outer surface of the capsule 49 containing the reactant 50 preferably comprises a selectively permeable membrane 54, chosen to permit the movement of water, carbon dioxide and ions therethrough, while preventing the passage of the reactant 50 or the resulting solid precipitate AgCl.

Once orally ingested, chloride ions (Cl⁻) and possibly hydrogen ions (H⁺) present in the patient's gastrointestinal tract pass through the membrane 54. The chloride ions (Cl⁻) bond with free silver ions (Ag⁺) to produce the precipitate AgCl by formula (i) disclosed previously. Bicarbonate ($HCO_3^-$), hydroxyl ($OH^-$) ions and carbonate ($CO_3^=$) ions released on the chloride ions (Cl⁻) bonding with the silver ions (Ag⁺), bond with free hydrogen ions (H⁺) within the capsule 49 or pass outwardly through the membrane 54 to bond with free hydrogen ions (H⁺) in the gastrointestinal tract to produce $CO_2$ and/or $H_2O$ (formulas (ii), (iii) and (vi) disclosed previously).

The combination of $Ag_2CO_3$ plus an anion exchange resin may further be used to permit the removal of unwanted ions such as sulfate ($SO_4^=$) and phosphate ($HPO_4^=$) in patients with kidney diseases or those lacking kidneys, for example by the reactions:

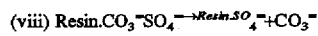

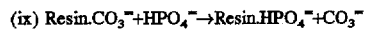

The $Ag_2CO_3$ composition for the treatment of kidney patients is still more preferably used in combination with existing treatments, such as those used to bond free potassium ions (K⁺). For example, one known treatment used to bond free K⁺ ions is presently marketed under the trade mark K-EXALATE. The composition of the present invention may be combined with treatments for binding K⁺ ions to both reduce the concentrations of free hydrogen ions (H⁺) and to improve the operation of potassium binders which by their operation release hydrogen ions (H⁺).

Insofar as the composition for the present invention acts to bind free hydrogen ions (H⁺) in a one-to-one stoichiometric ratio, it is possible to calculate the dosage or amount by weight of $Ag_2CO_3$ required to remove a given molar quantity of excess hydrogen ions (H⁺). It is therefore possible for an individual to calculate that X amount of $Ag_2CO_3$ should be ingested orally (or alternately rectally) on consuming 50 millilitres of wine, etc. as a counterbalance to an expected increase in potassium and/or hydrogen ions.

CLINICAL MODEL

A clinical model of the present invention has been undertaken with rats who had acute metabolic acidosis due to the ingestion of $NH_4Cl$, an acidifying salt. The rats had 10 mmol/Kg $NH_4Cl$ added to a fixed volume of drinking water which was totally consumed over several hours. This caused a fall in the plasma bicarbonate concentration from 29±1 mmol/l to 18±1 mmol/l on the next morning (9:00 h). The rats were then given 4 mEq of alkali by the oral route as $NaHCO_3$ or $Ag_2CO_3$. The control group received equimolar NaCl. Four hours later there was no appreciable difference in urine excretions, but as is apparent in Table 1, there was a significant rise in the plasma bicarbonate concentration of equal magnitude in the two alkali treatment groups.

TABLE 1

| Treatment Group | Plasma [HCO₃] mmol/l | | |
|---|---|---|---|
| | Pre | Post | Change |
| Control (n = 4) | 17 ± 1 | 19 ± 1 | 2.0 ± 1 |
| NaHCO₃ (n = 3) | 19 ± 1 | 25 ± 1 | 6.0 ± 1* |
| Ag₂CO₃ (n = 4) | 18 ± 1 | 24 ± 1 | 6.0 ± 1* |

In further experiments performed in rats, administration of $Ag_2CO_3$ via the stomach led to a loss of chloride and a stoichiometric gain in $HCO_3$ ions. There were no adverse effects, and the following major organs did not contain any radioactive Ag label (heart, brain, kidneys).

Although the disclosure describes and illustrates preferred embodiments and examples of the invention, the invention is not so limited. Many variations and modifications will now occur to those skilled in the art. For a definition of the invention reference may be made to the appended claims.

We claim:

1. A method of removing excess hydrogen ions in a patient's body fluid comprising,
   contacting said body fluid with a therapeutically effective amount of a hydrogen ion buffering means for bonding with free anions naturally present in said fluid and substituting therefore buffering ions which bond with said hydrogen ions to produce water and carbon dioxide molecules,
   wherein said therapeutically effective amount is an amount selected so as to lessen the likelihood of adverse health effects of excess hydrogen ions in said patient's body, and said buffering means comprising $Ag_2CO_3$.

2. A method of removing excess hydrogen ions in a patient's body fluid comprising,
   contacting said body fluid with hydrogen ion buffering means for bonding with free anions naturally present in said fluid and substituting therefore buffering ions which bond with said hydrogen ions to produce water and carbon dioxide molecules,
   wherein said step of contacting said body fluid further comprises orally ingesting said buffering means, and said buffering means comprising $Ag_2CO_3$.

3. A method of removing excess hydrogen ions in a patient's body fluid comprising the steps of:
   extracting said body fluid from said patient,
   contacting said body fluid with a hydrogen ion buffering means for bonding with free anions naturally present in said fluid and substituting therefore buffering ions with bond with said hydrogen ions to produce water and carbon dioxide molecules, and
   reintroducing said body fluid into said patient,
   wherein said buffering means comprising $Ag_2CO_3$.

4. A method of reducing the likelihood of adverse health effects of excess hydrogen ions in an individual resulting from a medical condition selected from the group consisting of a heart attack, poor renal function and acute renal failure, said method including the step of,
   contacting a body fluid of said individual with a therapeutically effective amount of buffering means comprising $Ag_2CO_3$, said buffering means for bonding with free chloride ions naturally present in said body fluid and substituting therefore buffering ions selected from the group consisting of carbonate ions and bicarbonate ions, and wherein said buffering ions bond with said hydrogen ions to produce water and carbon dioxide molecules.

5. The method of claim 1 wherein said body fluid is contacted with said buffering means in vivo.

6. The method of claim 1 wherein said body fluid is contacted with said buffering means in vitro.

7. The method of claim 1 wherein said buffering means further comprises a carrier selected from the group consisting of an anion exchanger on dextran, an anion exchanger on agarose, an anion exchanger on cellulose and an anion exchanger on polystyrene.

8. The method of claim 1 wherein said free anions comprise chloride ions.

9. The method of claim 7 wherein said free anions comprise chloride ions.

10. The method of claim 9 wherein said composition further includes an anion exchange resin for bonding with sulphate or phosphate anions naturally present in said fluid and substituting therefore carbonate ions or bicarbonate ions.

11. The method of claim 1 wherein said buffering means is administered to said patient in conjunction with a composition for binding free potassium ions.

12. The method of claim 1 wherein said buffering means is encapsulated within a selectively permeable membrane which permits ion flow between said patient's body fluid and said buffering means while preventing movement of said buffering means into said patient.

13. The method of claim 12 wherein said selectively permeable membrane is a natural cellulose membrane.

14. The method of claim 2 wherein said buffering means is administered to said patient in conjunction with a composition for binding free potassium ions.

15. The method of claim 2 wherein said buffering means further comprises a carrier selected from the group consisting of an anion exchanger on dextran, an anion exchanger on agarose, an anion exchanger on cellulose and an anion exchanger on polystyrene.

16. The method of claim 3 wherein said buffering means further comprises a carrier selected from the group consisting of an anion exchanger on dextran, an anion exchanger on agarose, an anion exchanger on cellulose and an anion exchanger on polystyrene.

17. The method of claim 2 wherein said buffering means is encapsulated within a selectively permeable membrane which permits ion flow between said patient's body fluid and said buffering means while preventing movement of said buffering means into said patient.

18. The method of claim 3 wherein said buffering means is encapsulated within a selectively permeable membrane which permits ion flow between said patient's body fluid and said buffering means while preventing movement of said buffering means into said patient.

19. The method as claimed in claim 1 where said step of contacting said body fluid is performed to buffer increased hydrogen ion concentrations resulting from a medical condition selected from the group consisting of a heart attack, poor renal function and acute renal failure.

20. The method as claimed in claim 3 wherein prior to said step of reintroducing said fluid into said patient, said fluid is passed through a selectively permeable membrane which prevents movement of said buffering means therethrough.

* * * * *